(12) United States Patent
Wang

(10) Patent No.: US 11,103,728 B2
(45) Date of Patent: *Aug. 31, 2021

(54) METHODS AND SYSTEMS FOR IRRADIATION BASED ON A FLUENCE MAP

(71) Applicant: SHANGHAI UNITED IMAGING HEALTHCARE CO., LTD., Shanghai (CN)

(72) Inventor: Weiyuan Wang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 52 days.

This patent is subject to a terminal disclaimer.

(21) Appl. No.: 16/587,538

(22) Filed: Sep. 30, 2019

(65) Prior Publication Data

US 2020/0023199 A1    Jan. 23, 2020

Related U.S. Application Data

(63) Continuation of application No. 15/394,902, filed on Dec. 30, 2016, now Pat. No. 10,434,334.

(30) Foreign Application Priority Data

Dec. 31, 2015    (CN) .......................... 201511030923.2

(51) Int. Cl.
    *A61N 5/10*    (2006.01)
(52) U.S. Cl.
    CPC ......... *A61N 5/1045* (2013.01); *A61N 5/1036* (2013.01); *A61N 2005/1087* (2013.01)

(58) Field of Classification Search
    CPC .............. A61N 5/1045; A61N 5/1036; A61N 2005/1087; A61N 5/1031; A61N 5/1048
    See application file for complete search history.

(56) References Cited

U.S. PATENT DOCUMENTS 6,266,393 B1    7/2001    Ein-Gal
10,434,334 B2 *  10/2019  Wang .................. A61N 5/1045

FOREIGN PATENT DOCUMENTS

| CN | 104307115 A | 1/2015 |
| WO | 2011121037 A1 | 10/2011 |

OTHER PUBLICATIONS

First Office Action in Chinese Application No. 201511030923.2 dated Dec. 4, 2017, 10 pages.

* cited by examiner

*Primary Examiner* — Courtney D Thomas
(74) *Attorney, Agent, or Firm* — Metis IP LLC

(57) ABSTRACT

A method for irradiation based on a fluence map includes determining a shield type of each row of a fluence map. The method also includes determining, for each of the two rows, a movement curve indicating a relationship between an irradiation dose in the each of the two rows and a moving position of a leaf pair corresponding to the each of the two rows. The method further includes determining an initial irradiation dose for each of the movement curves and synchronizing one of the movement curves based on the shield types of the two rows. The method also includes selecting at least one irradiation dose of at least one point on an irradiation dose axis and generating a control point according to the selected irradiation dose.

20 Claims, 15 Drawing Sheets

METHODS AND SYSTEMS FOR IRRADIATION BASED ON A FLUENCE MAP

CROSS-REFERENCE TO RELATED APPLICATIONS

This application is a continuation of U.S. application Ser. No. 15/394,902, filed on Dec. 30, 2016, which claims priority to Chinese Application No. 201511030923.2, filed on Dec. 31, 2015, the contents of each of which are hereby incorporated by reference in its entirety.

TECHNICAL FIELD

The present disclosure generally relates to methods and systems for irradiation, and more particularly, methods and systems for irradiation according to a fluence map.

BACKGROUND

Along with development of theories such as radiophysics, radiobiology, clinical oncology, etc., especially with continuous development of medical imaging apparatus and computer technology, radiotherapy (RT) technology has been continuously developed, and meets more clinic requirements. It is a great improvement from the conventional RT technology to 3D conformal radiation therapy (3DCRT). Since then, RT technology has entered into an era of precise RT, and incidence rate of partial recurrence of tumor and complication of normal tissue has been largely reduced. Intensity-modulated radiation therapy (IMRT) developed based on 3DCRT can conform to target better and protect organs at risk (OAR) around the target better, especially when the OAR is positioned in a concave target.

The IMRT, it may include one or more steps: dividing a beam field into a plurality of segment fields, giving these segment fields different weights, and generating an uneven intensity distribution in the beam field. In this way, beam fluence aimed at the OAR may be reduced while beam fluence aimed at other portion of the target may be increased. In a radiotherapy apparatus, a desired dose distribution may be implemented by controlling a multileaf collimator (MLC) according to a fluence map. An MLC may include a plurality of leaf pairs. Each leaf pair may include a left leaf and a right leaf. The left leaf may be positioned within a cage on the left, and the right leaf may be positioned within a cage on the right. The left leaf and the right leaf may extend out of the corresponding cages. The lengths of extension of the left leaf and/or the right leaf may be restrained. Difference between the longest length of extension and the shortest length of extension of the left leaf or the right leaf may be referred to as the largest leaf-span.

In a radiotherapy, if a tumor has large coverage areas and complex shapes (e.g., head-neck tumors), the fluence map obtained by modulating intensity may usually have large coverage areas and complex shapes. If the horizontal distance between initial and/or terminal points in rows to beirradiated is greater than the largest leaf span of an MLC, irradiation of the initial and/or terminal points in the rows may not be started and/or completed simultaneously.

At present, a field-dividing method may be used to solve the problems. The method may be implemented by dividing a beam field into a plurality of segment fields. During irradiation, jaws and an MLC moves to a first segment field, and the first segment field may be irradiated firstly. When the irradiation of the segment field is completed, the first segment field may be closed. Simultaneously, the jaws and the MLC may move to a second segment field, and the second segment field may be irradiated. The above operations may be repeated until irradiation of all segment fields being completed. The jaws may include parallel jaws (the movement direction of the jaws may be parallel to the movement direction of the MLC) and perpendicular jaws (the movement direction of the jaws may be perpendicular to the movement direction of the MLC). The jaws may be used to define a range of a beam field.

However, the field-diving method may have some defects. In the method, a beam field may be divided into a plurality of segment fields. Irradiation of the plurality of segment fields may increase total doses. For example, the total doses may increase to approximately two times than original minimum total doses when one beam field is added. Besides, if irradiation of a segment field is completed, the jaws and the MLC may move to next segment field. The moving of the jaws and the MLC may take time. The time spent on the moving may be referred as a 'build-up time'. The total irradiation time may be increased accordingly. Further, there may be penumbra in a segment field, Thus, doses delivered at the edge of adjacent segment fields may be inaccurate.

SUMMARY

In one aspect of the present disclosure, a method for irradiation based on a fluence map is provided. The method may include determining a shield type of each row of the fluence map. The method may also include determining, for each of the two rows, a movement curve indicating a relationship between an irradiation dose in the each of the two rows and a moving position of a leaf pair corresponding to the each of the two rows. The method may further include determining an initial irradiation dose for each of the movement curves and synchronizing one of the movement curves based on the shield types of the two rows. The method may also include selecting at least one irradiation dose of at least one point on an irradiation dose axis and generating a control point according to the selected irradiation dose.

In some embodiments, the shield type of the each of two rows may include at least one of the following types: shielded at a start of an irradiation and shielded at an end of the irradiation (SS-ES); not shielded at the start of an irradiation and shielded at the end of the irradiation (NSS-ES); shielded at the start of an irradiation and not shielded at the end of the irradiation (SS-NES); or not shielded at the start of an irradiation and not shielded at the end of the irradiation (NSS-NES).

In some embodiments, the method may further include determining whether at least one of the shield types of the two rows is NSS-ES or NSS-NES. If at least one of the shield types of the two rows is NSS-ES or NSS-NES, an initial irradiation dose of the movement curve of the row of the two rows having NSS-ES or NSS-NES shield type may be set to zero.

In some embodiments, the method may further include smoothing the movement curves.

In some embodiments, the synchronization of the one of the movement curves may include determining whether a terminal irradiation point in one of the two rows needs to be shielded at an end of an irradiation. If the terminal irradiation point in one of the two rows needs to be shielded at the end of the irradiation, the movement curve corresponding to the one of the two rows may be synchronized with the movement curve corresponding to the other of the two rows.

The movement curve corresponding to the one of the two rows may be adjusted based on a result of the synchronization.

In some embodiments, the synchronization of the one of the movement curves may include determining whether an initial irradiation point in one row of the two rows needs to be shielded at a start of the irradiation. If the initial irradiation point in the one row of the two rows needs to be shielded at the start of the irradiation, the movement curve corresponding to the one of the two rows may be synchronized with the movement curve corresponding to the other of the two rows. The movement curve corresponding to the one of the two rows may be adjusted based on a result of the synchronization.

In some embodiments, if the initial irradiation point in one of the two rows needs to be shielded at the start of the irradiation, an initial irradiation dose of the movement curve corresponding to the one of the two rows may be determined.

In some embodiments, the selection of the irradiation dose of the at least one point on the irradiation dose axis may include determining weights of a plurality of points on the irradiation dose axis, and then selecting at least one irradiation dose according to the weights of the plurality of points on the irradiation dose axis.

In some embodiments, the generation of the control point according to the selected irradiation dose may include determining whether a leaf pair reaches the selected irradiation dose. If a leaf pair reaches the selected irradiation dose, a control point corresponding to the irradiation dose may be generated.

In some embodiments, a distance between a first point in a first row of the two rows of the fluence map and a second point in a second row of the two rows of the fluence map may be greater than a leaf-span of a collimator.

In some embodiments, the first point or the second point may be a leftmost or rightmost point of the corresponding row.

In another aspect of the present disclosure, a system for irradiation based on a fluence map is provided. The system may include a processor. The processor may be configured to determine a shield type of each row of the fluence map The processor may also be configured to determine, for each of the two rows, a movement curve indicating a relationship between an irradiation dose in the each of the two rows and a moving position of a leaf pair corresponding to the each of the two rows. The processor may further be configured to determine an initial irradiation dose for each of the movement curves and synchronizing one of the movement curves based on the shield types of the two rows. The processor may also be configured to select at least one irradiation dose of at least one point on an irradiation dose axis and generate a control point according to the selected irradiation dose.

In some embodiments, the processor may further be configured to determine whether at least one of the shield types of the two rows is NSS-ES or NSS-NES. If at least one of the shield types of the two rows is NSS-ES or NSS-NES, an initial irradiation dose of the movement curve of the row of the two rows having NSS-ES or NSS-NES shield type may be set to zero.

In some embodiments, the processor may further be configured to smooth the movement curves.

In another aspect of the present disclosure, a computer readable storage medium, including executable instructions is provided. At least one of the executable instructions may implement a method, and the method may include determining a shield type of each row of the fluence map. The method may also include determining, for each of the two rows, a movement curve indicating a relationship between an irradiation dose in the each of the two rows and a moving position of a leaf pair corresponding to the each of the two rows. The method may further include determining an initial irradiation dose for each of the movement curves and synchronizing one of the movement curves based on the shield types of the two rows. The method may also include selecting at least one irradiation dose of at least one point on an irradiation dose axis and generating a control point according to the selected irradiation dose.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
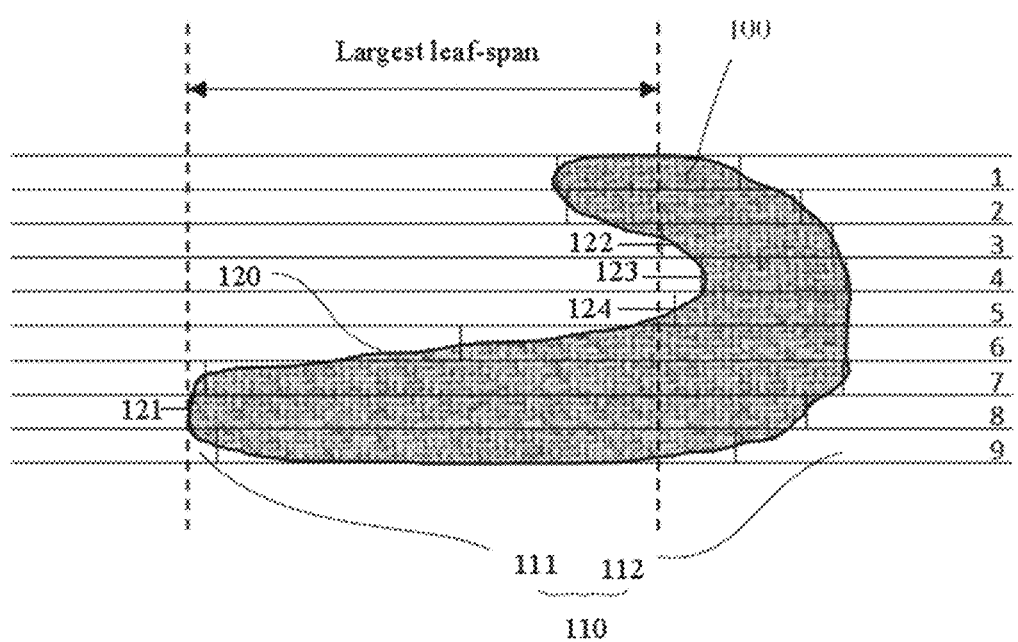
FIG. 1 is a schematic diagram of an exemplary fluence map of a subject according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirits and scope of the present disclosure. Thus, the present disclosure is not limited to the embodiments shown, but to be accorded the widest scope consistent with the claims.

It will be understood that the term "system," "unit," "module," and/or "block" used herein are one method to distinguish different components, elements, parts, section or assembly of different level in ascending order. However, the terms may be displaced by other expression if they may achieve the same purpose.

It will be understood that when a unit, module or block is referred to as being "on," "connected to" or "coupled to" another unit, module, or block, it may be directly on, connected or coupled to the other unit, module, or block, or intervening unit, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

In order to clearly understand the objective, features, and advantages of the present disclosure, the specific embodiments of the present disclosure are described in combination with the companying drawings as follows.

In the following description, more details are described for comprehensively understanding the present invention. The present disclosure may also be implemented using other embodiments that may be different from the embodiments described herein. Therefore, the present disclosure may not be limited to the specific embodiments disclosed hereinafter.

In some embodiments of the present disclosure, a method and system for irradiation based on a fluence map are disclosed. The method and the system may be applied to a radiotherapy apparatus. The method and the system for irradiation based on a fluence map may not need to divide a beam field.

FIG. 1 is a schematic diagram of an exemplary fluence map corresponding to a subject according to some embodiments of the present disclosure. In some embodiments, the fluence map may represent a desired intensity profile of particle beams and/or energies that are delivered to a subject in an irradiation process. The particle beams and/or energies may include α-rays, β-rays, γ-rays, X-rays, electron beams, proton beams, other particle beams, or the like, or any combination thereof. The subject may be a tissue, an organ, a tumor, etc. As shown in FIG. 1, a fluence map 100 may have a number of rows (e.g., nine rows, which labeled with row numbers, shown in FIG. 1). It can be understood that the fluence map 100 is merely a portion of an actual fluence map. There may be one leaf pair 110 corresponding to each row to block and/or control the irradiation so that the subject may receive a desired dose as illustrated in the fluence map 100. As there are nine rows in the fluence map 100, nine leaf pairs may be configured. Each leaf pair may include a left leaf 111 and a right leaf 112. The left leaf 111 may be positioned within a cage on the left, and the right leaf 112 may be positioned within a cage on the right. In some embodiment, the left leaf 111 and the right leaf 112 may extend out of the corresponding cages. The lengths of extension of the left leaf 111 and/or the right leaf 112 may be restrained. In some embodiments, difference between the longest length of extension and the shortest length of extension of the left leaf 111 or the right leaf 112 may be referred to as the largest leaf-span (shown in FIG. 1). It should be noted that "leaf-span" and "largest leaf-span" unless stated otherwise shall have the similar meaning in present disclosure. In some embodiments, the horizontal distance between leftmost points (or rightmost points) in two rows of the fluence map 100 may be greater than the largest leaf-span. For example, with respect to the left contour 120 of the fluence map 100, a point 121 in Row 8 is leftmost, and the horizontal distance between the point 121 in Row 8 and a point 122 in Row 3 (or a point 123 in Row 4, or a point 124 in Row 5) may be greater than the largest leaf-span. As described elsewhere in the present disclosure, a beam field may be created by passing beams through an aperture. The aperture may be formed by leaf pairs. When the horizontal distance between two leftmost points (or rightmost points) in two rows of a fluence map is greater than the largest leaf-span, it may be hard to irradiate a subject according to the fluence map 100 without dividing the beam field.

Figure 2A:
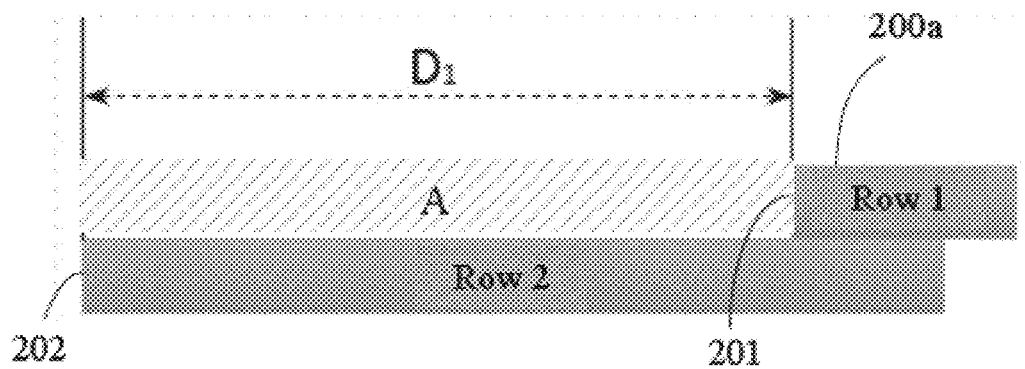
FIGS. 2(a) and 2(b) illustrate exemplary diagrams of horizontal distances between the leftmost and rightmost points of two rows according to some embodiments of the present disclosure.
Figure 2B:
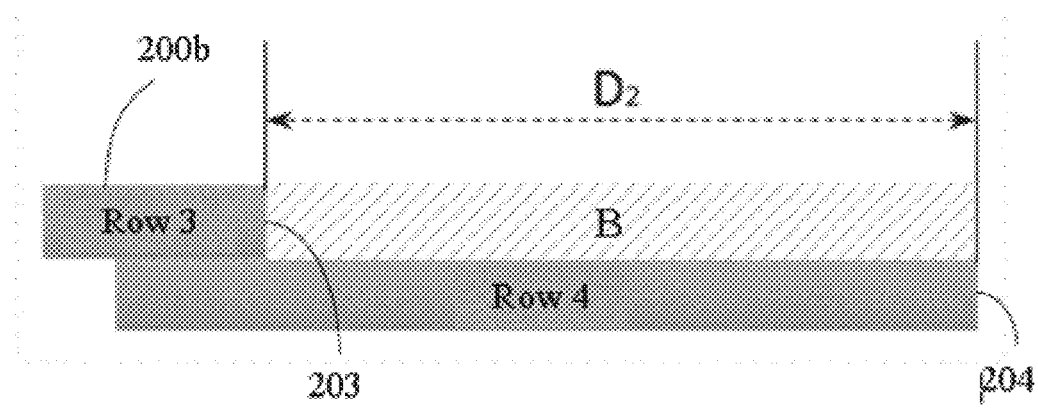

FIGS. 2(a) and 2(b) illustrate exemplary diagrams of horizontal distances between the leftmost and rightmost points of two rows, respectively, according to some embodiments of the present disclosure. As shown in FIG. 2(a), a distance $D_1$ may refer to a horizontal distance between the leftmost point 201 in Row 1 and the leftmost point 202 in Row 2 of the fluence map 200a. During a dynamic IMRT, the distance $D_1$ may refer to a horizontal distance between the initial irradiation point (the leftmost point 201) in Row 1 and the initial irradiation point (the leftmost point 202) in Row 2. Irradiation of Row 1 and Row 2 cannot be started simultaneously if the distance $D_1$ is greater than the largest leaf-span of an MLC. For example, the leaves may move from left to right. When the initial irradiation point 201 in Row 1 is irradiated, no point in Row 2 should be irradiated within the leaf-span. Thus, an area A corresponding to the distance $D_1$ in Row 1 may be shielded in order to block and reduce the extra irradiation. If the area A is not shielded properly, a certain amount of irradiation may leak through a gap between the leaf pair in Row 1 and bring extra irradiation. Detailed descriptions of the leakage and shielding may be found elsewhere in the present disclosure. The area A may be shielded by a trailing jaw. As shown in FIG. 2(b), a distance $D_2$ may refer to a horizontal distance between the rightmost point 203 in Row 3 and the rightmost point 204 in Row 4 of the fluence map 200b. During a dynamic IMRT, the distance $D_2$ may refer to a horizontal distance between the terminal irradiation point (the rightmost point 203) in Row 3 and the terminal irradiation point (the rightmost point 204) in Row 4. Similarly, irradiation of Row 3 and Row 4 should not complete simultaneously if the distance $D_2$ is greater than a largest leaf-span of an MLC. For example, the leaves may move from left to right. When the leaves corresponding to Row 3 moves to the terminal irradiation point 203 of Row 3, irradiation of points in Row 3 is completed, but there may still be some points in Row 4 that need to be irradiated. Thus, an area B corresponding to the distance $D_2$ in Row 3 may be shielded in order to reduce and block extra irradiation. The area B may be shielded by a leading jaw. Particularly, the movement direction of the leading jaw and the trailing jaw may be parallel to the movement direction of leaves of the MLC. Thus, the leading and the trailing jaws are referred to as parallel jaws. In some embodiments of the present disclosure, the parallel jaws may be used to assist an MLC during an irradiation.

Figure 3:
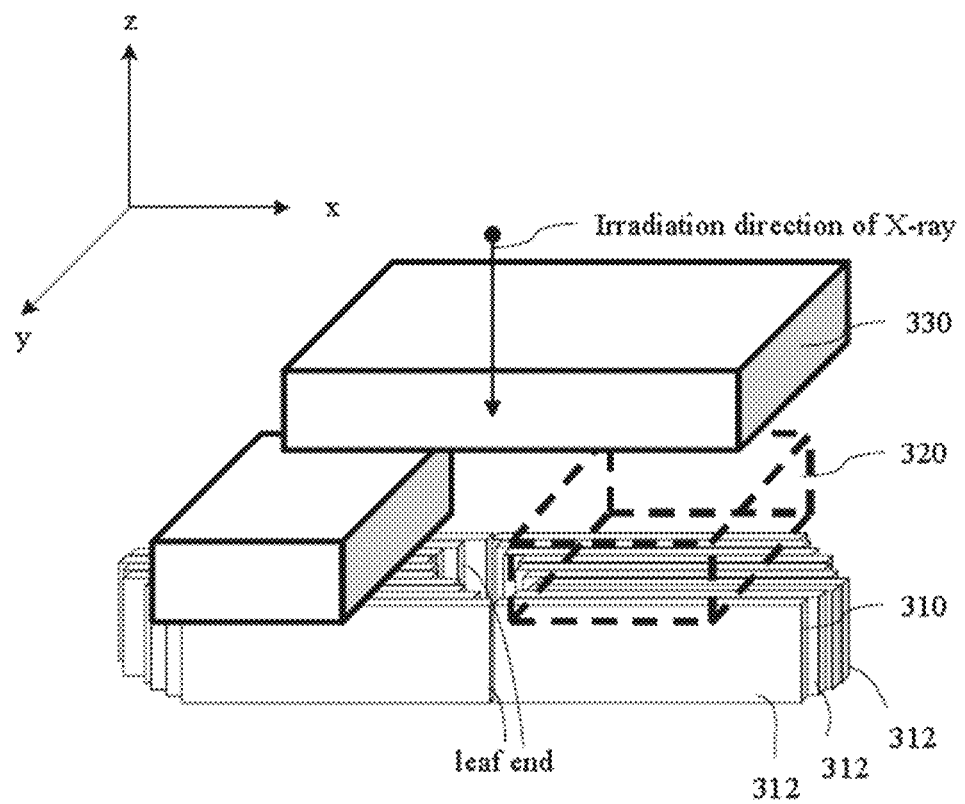
FIG. 3 is a perspective view of exemplary jaws and an exemplary MLC according to some embodiments of the present disclosure.

FIG. 3 is a perspective view of exemplary jaws and an MLC according to some embodiments of the present disclosure. As shown in FIG. 3, the MLC 310 may include one or more leaf pairs 312. The leaf pairs 312 may move along x-direction as shown in FIG. 3. In some embodiments, two leaves of each leaf pair 312 may be closed (e.g., the leaf ends touch or are close to each other) or opened (e.g., an aperture is formed). The distance between the leaves may be controlled by the MLC 310. In some embodiments, to avoid collision, a gap may exist between the leaves of leaf pair 310 when they are closed. Parallel jaws 320 may move along the x-direction (e.g., moving in parallel along with the movement direction of the leaf pairs 312). Similarly, perpendicular jaws 330 may move along the y-direction (e.g., moving perpendicularly to the movement direction of the leaf pairs 312). In some embodiments, there may be two parallel jaws 320 and two perpendicular jaws 330. As described elsewhere in the present disclosure, the parallel jaws may include a trailing jaw and a leading jaw. In some embodiments, if the movement of leaves is changed, positions of the trailing jaw and the leading jaw may be swapped and the movement of the jaws may be changed. In some embodiments, one or more of the jaws may be omitted.

As shown in FIG. 3, the leaf pairs 312 of the MLC 310 may be shielded by the parallel jaws 320 and/or the perpendicular jaws 330. In some embodiments, the jaws may define a range of a beam field. For example, the range of the beam field may be defined as a rectangle by the parallel jaws 320 and/or the perpendicular jaws 330. Furthermore, a contour of the beam field that corresponds to the fluence map may be further defined by the leaf pairs 312 of the MLC 310.

As described above, a gap may exist between the leaves of leaf pair 312 when they are closed. If the gap of the leaf pair is exposed in the beam field for a long time, a dose delivered to the area of an irradiated subject (e.g., a tumor) near the gap may be higher than desired. In some embodiments of the present disclosure, the parallel jaws 320 may shield leaf pairs to block or absorb extra irradiation. As described elsewhere in the disclosure, a horizontal distance between two leftmost points (or rightmost points) in two rows of a fluence map may be greater than the leaf-span of the MLC, as illustrated in FIG. 1. In other words, when a point in a first row is irradiated, no point in a second row should be irradiated within the leaf-span. In this case, the parallel jaws 320 may shield the gap of the leaf pair in the second row so that the dose delivered to the area of the irradiated subject around the gap may be kept to a desired amount.

Figure 15:
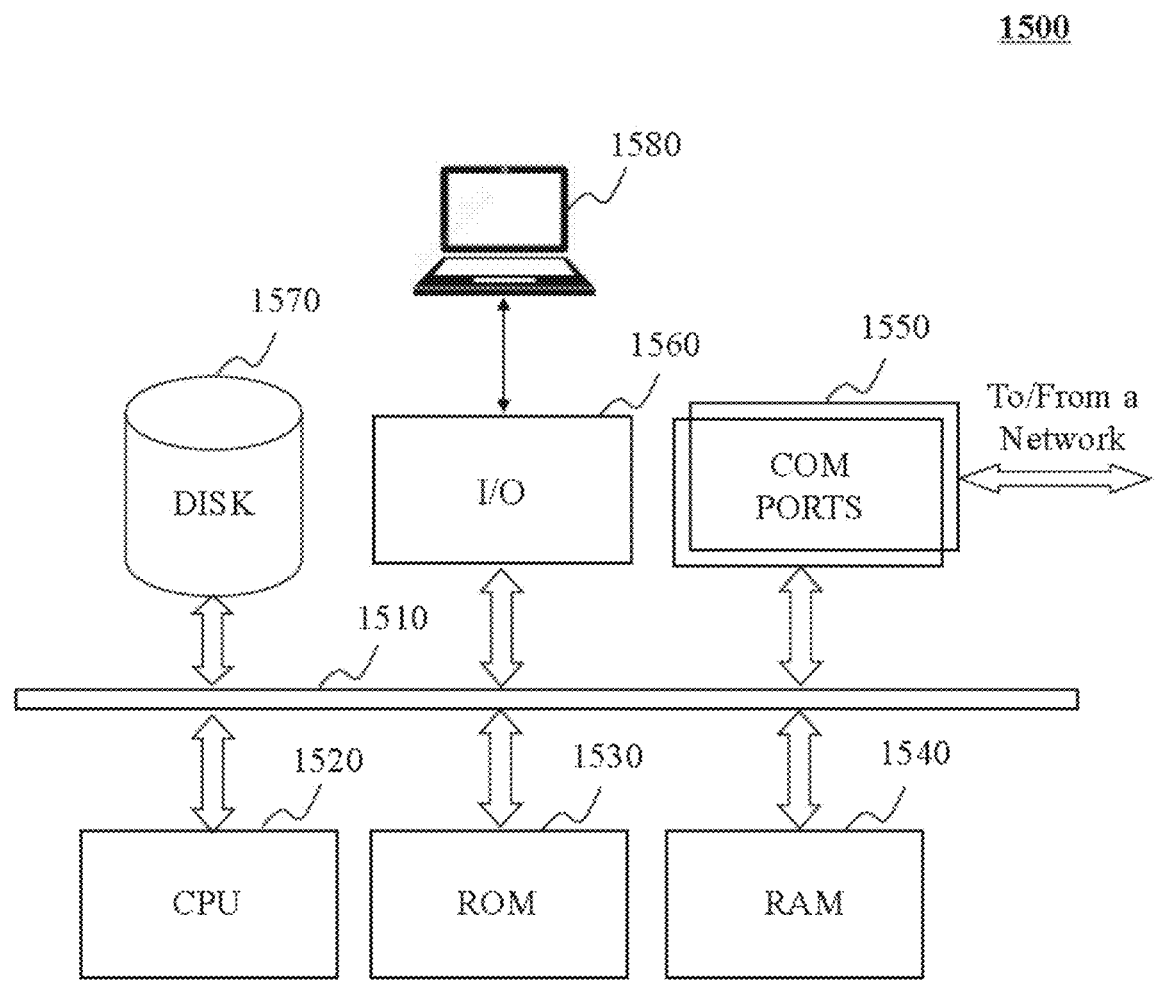
FIG. 15 is a schematic diagram illustrating exemplary hardware and software components of a computing device.

FIG. 15 is a schematic diagram illustrating exemplary hardware and software components of a computing device 1500 in communication with the MLC 310 and configured to control the movement of jaws and leaves.

The computing device 1500 may include, among other things, COM ports 1550 connected to and from a network connected thereto to facilitate data communications. The computing device 1500 may also include a central processing unit (CPU) 1520, in the form of one or more processors, for executing program instructions, which may be stored in a storage device (e.g., disk 1570, ROM 1530, and RAM 1540). When executing the program instructions, the CPU 1520 is configured to cause computing device 1500 to perform the functions described in this disclosure. In some embodiments, the computing device 1500 may include other type of processors such as an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a controller, a microcontroller unit, a reduced instruction-set computer (RISC), a microprocessor, or the like, or any combination thereof. The exemplary computer platform may include an internal communication bus 1510, program storage and data storage of different forms, for example, a disk 1570, and a read only memory (ROM) 1530, or a random access memory (RAM) 1540, for various data files to be processed and/or transmitted by the computer. The exemplary computer platform may also include executable program instructions stored in the ROM 1530, RAM 1540, and/or other type of non-transitory storage medium to be executed by the CPU 1520. The methods and/or processes of the present disclosure may be implemented as the program instructions. For example, the movement of the jaws or leaf pairs in the present disclosure may be implemented by computing device 1500 as the program instructions. Computing device 1500 also includes an I/O component 1560, supporting input/output between the computer and other components therein such as user interface elements 1580. Computing device 1500 may also receive programming and data via network communications.

Merely for illustration, only one CPU and/or processor is described in the computing device 1500. However, it should be noted that the computing device 1500 in the present disclosure may also include multiple CPUs and/or processors, thus operations and/or method steps that are performed by one CPU and/or processor as described in the present disclosure may also be jointly or separately performed by the multiple CPUs and/or processors. For example, a first processor may control the movement of the jaws and a second processor may control the movement of the leaf pairs. Alternatively, the first processor and the second processor may jointly control the movements of the leaf pairs and the jaws.

Figure 11:
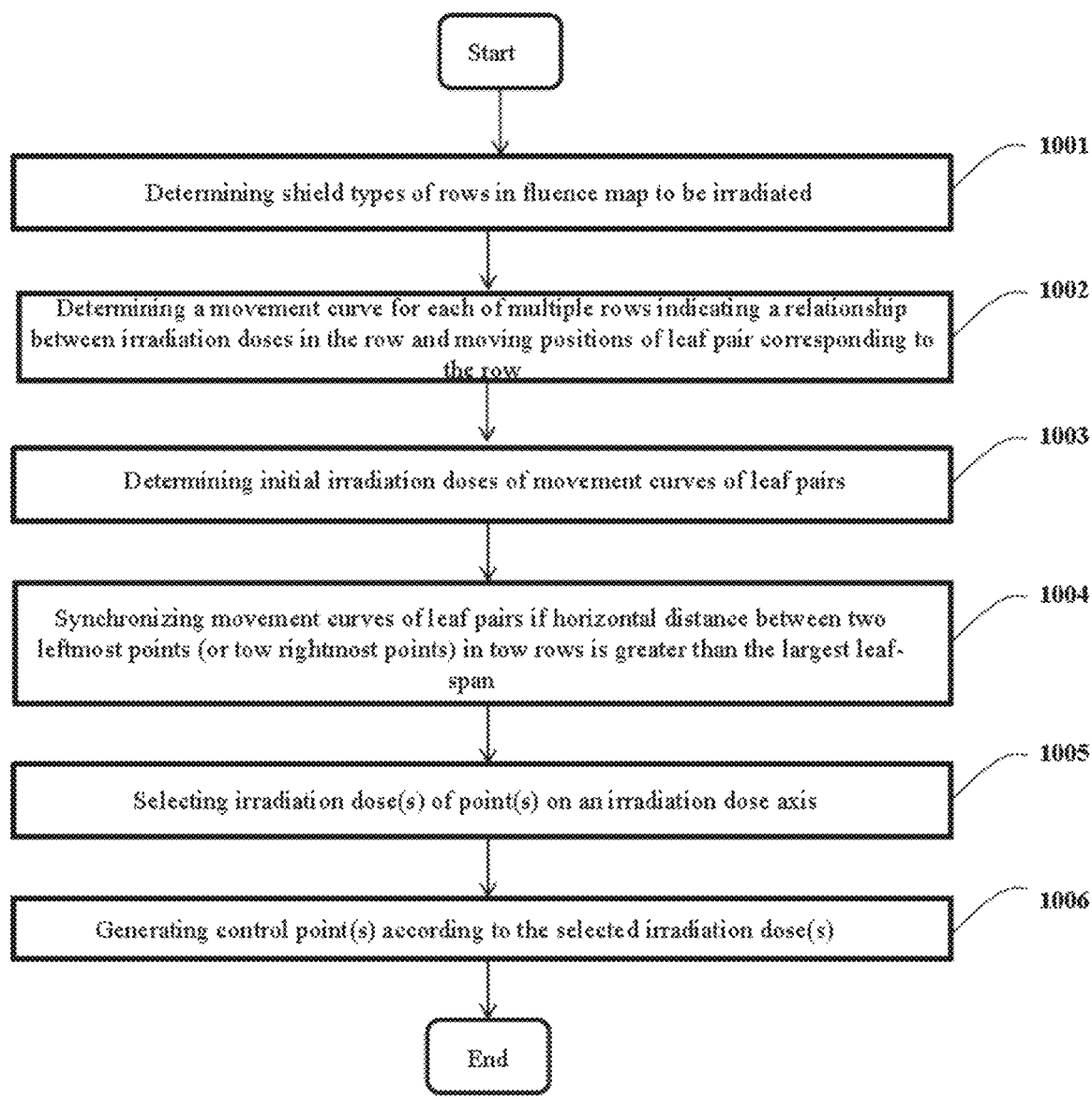
FIG. 11 is a flowchart of an exemplary irradiation method based on a fluence map according to some embodiments of the present disclosure.

FIG. 11 is a flowchart of an exemplary irradiation method based on a fluence map according to some embodiments of the present disclosure. In step 1001, shield types of the rows in the fluence map that need to be irradiated may be determined. In some embodiments, the CPU 1520 of the MLC 310 may determine the shield types. In some embodiments, the disk 1570, ROM 230, and/or RAM 240 may store the determined shield types. In some embodiments, the computing device 1500 may transmit the determined shield types to a user via the I/O component 1560. The rows that need to be irradiated may be classified into one of four shield types based on whether a row needs to be shielded at the start and/or the end of irradiation. The four shield types may include, for example, shielded at the start and shielded at the end (SS-ES), not shielded at the start and shielded at the end (NSS-ES), shielded at the start and not shielded at the end (SS-NES), and not shielded at the start and not shielded at the end (NSS-NES). In some embodiments, the shield types of the rows are determined according to a relationship between the outer contour of the fluence map and the largest leaf-span. For example, the leaves may move from left to right, and if the horizontal distance between two points in two rows on the left contour (or referred to as the leftmost points in the rows) is greater than the largest leaf-span, the row that is later irradiated may be shielded at the start of the irradiation. If the horizontal distance between two points in two rows on the right contour (or referred to as the rightmost points in the rows) is greater than the largest leaf-span, the row that earlier completes irradiation may be shielded at the end of the irradiation. Take the contour of the fluence map in FIG. 1 as an example. In the left contour 120 of the fluence map 100, a point 121 in Row 8 is leftmost, and the horizontal distance between the point 121 in Row 8 and a point 122 in Row 3 (or a point 123 in Row 4, or a point 124 in Row 5) may be greater than the largest leaf-span. In this case, the shield type of the fluence map in FIG. 1 may be determined as SS-NES.

In step 1002, a movement curve for each of multiple rows, indicating a relationship between irradiation doses in a row and the moving positions of the leaf pair(s) in the corresponding row may be determined. In some embodiments, the CPU 1520 may determine the movement curve. In some embodiments, the disk 1570, ROM 230, and/or RAM 240 may store the determined movement curve. In some embodiments, the computing device 1500 may transmit the determined movement curve to a user via the I/O component 1560.

The movement curve may be referred to as a one-dimensional (1D) leaf trajectory. In the 1D leaf trajectory, the horizontal distance between points in rows is not compared with the largest leaf-span. Detailed description of the movement curve is described elsewhere in this disclosure in connection with FIG. 6.

In step 1003, initial irradiation doses corresponding to the movement curves of the leaf pairs may be determined. In some embodiments, the CPU 1520 or other calculation components of the MLC 310 may determine the initial irradiation doses. In some embodiments, a user may provide the initial irradiation doses via the I/O component 1560. Each movement curve may include a left contour and a right contour that correspond to the movement trajectories of a left leaf and a right leaf respectively. The initial irradiation doses corresponding to the movement curves may be different for rows with different shield types. The initial irradiation dose corresponding to a movement curve may be set to 0 for a row that is not shielded at the start of irradiation. The initial irradiation dose corresponding to a movement curve may not be set to 0 for a row that is shielded at the start of irradiation, but may be determined by a synchronization process. The detailed descriptions of the synchronization and determination may be found elsewhere in present disclosure. For example, the initial irradiation dose corresponding to the movement curve is set to 0 for Row 8 in FIG. 1, and the initial irradiation dose corresponding to the movement curve is not set to 0 for Row 4 in FIG. 1.

In step 1004, the movement curves of leaf pairs may be synchronized if a horizontal distance between two leftmost points (or two rightmost points) in two rows is greater than the largest leaf-span. In some embodiments, the CPU 1520 of the MLC 310 may perform the synchronization process. If the horizontal distance between any two leftmost points (or two rightmost points) is equal to or less than the largest leaf-span, step 1005 may be performed. If the horizontal distance between two leftmost points (or rightmost points) in rows of a fluence map is greater than a leaf-span, the corresponding rows (e.g., Row 4 in FIG. 6, Row 6 in FIG. 7, etc.) may be shielded at the start and/or end of irradiation. In this case, the movement curves of the leaf pairs may be synchronized. The synchronization process is described elsewhere in this disclosure in connection with FIG. 12.

In step 1005, irradiation dose(s) of point(s) on an irradiation dose axis (the vertical axis in FIG. 6, etc.) may be determined. In some embodiment, the irradiation dose may be expressed by monitor unit (MU). One MU is approximately 0.01 Gray (Gy). One Gray may refer to that 1 kg of an irradiated subject absorbs 1 Joule of energy.

A minimum resolution (e.g., 0.1MU) on an irradiation dose axis may be determined. In the synchronized movement curves (e.g., shown in FIG. 7(c) or FIG. 8), weights corresponding to some or all points on the irradiation dose axis may be obtained. In some embodiments, the CPU 1520 of the MLC 310 may determine the weights. In some embodiments, a user may provide the weights via the I/O component 1560. For a point on the irradiation dose axis, the weight of the point may be a sum of weights of the movement curves at the irradiation dose of the point. If a movement curve has an obvious turning point at a certain irradiation dose, such as $MU_{maxt}$ shown in FIG. 8(a), a higher weight may be given to the point on the irradiation dose axis at the corresponding irradiation dose. Alternatively, if a turning point of the movement curve is not obvious, a smaller weight may be given to the point on the irradiation dose axis at the corresponding irradiation dose. Further, if the movement curve does not have any obvious turning point (e.g., the movement curve is smooth), a weight 0 may be given to the point on the irradiation dose axis at the corresponding irradiation dose.

There may be numerous candidate irradiation doses on the irradiation dose axis. A certain number of irradiation doses may be selected from the candidate irradiation doses using Matthew effect (a rule of merit-based enrollment) according to the weights given to the points of the irradiation dose axis corresponding the irradiation doses. A list including the selected irradiation doses (each of which corresponds to a point on the irradiation dose axis) may be generated. In some embodiments, the disk 1570, ROM 230, and/or RAM 240 may store the codes or instructions of the algorithms (e.g., the Matthew effect). In some embodiments, the CPU 1520 of the MLC 310 may select the irradiation doses from candidate irradiation doses. In some embodiments, the disk 1570, ROM 230, and/or RAM 240 may also store the selected irradiation doses or the list of the doses. Alternatively or additionally, the computing device 1500 may transmit the selected irradiation doses and/or the list of the doses to a user via the I/O component 1560.

In step 1006, control point(s) may be generated according to the selected irradiation dose(s). In some embodiments, the CPU 1520 of the MLC 310 may perform the generation process of the control point(s). In some embodiments, the disk 1570, ROM 230, and/or RAM 240 may also store the generated control point(s). Alternatively or additionally, the computing device 1500 may transmit the generated control point(s) to a user via the I/O component 1560.

As described above, each selected irradiation dose in the list may correspond to a point on the irradiation dose axis.

When each leaf reaches selected irradiation dose(s), control point(s) corresponding to the irradiation dose(s) may be generated accordingly.

Figure 4A:
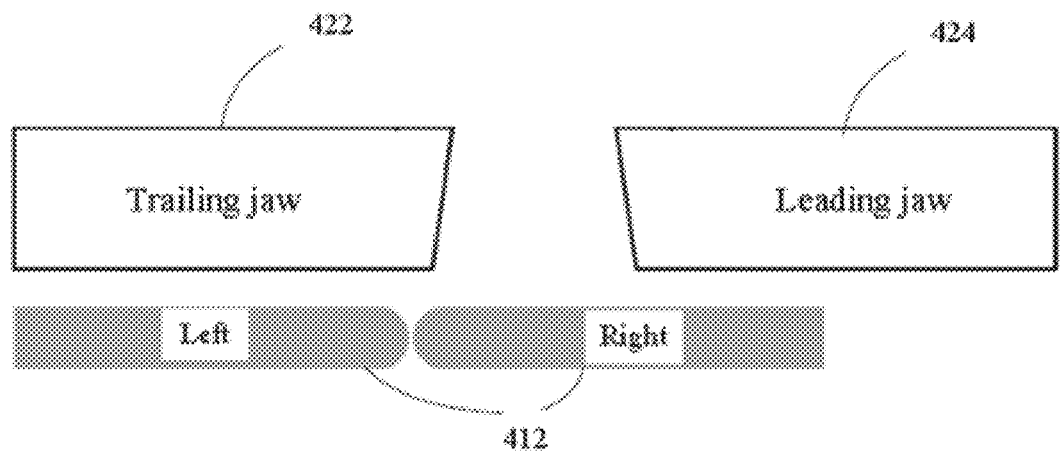
FIGS. 4(a)-4(c) illustrate exemplary relative positions of jaws and a leaf pair of an MLC according to some embodiments of the present disclosure.
Figure 4B:
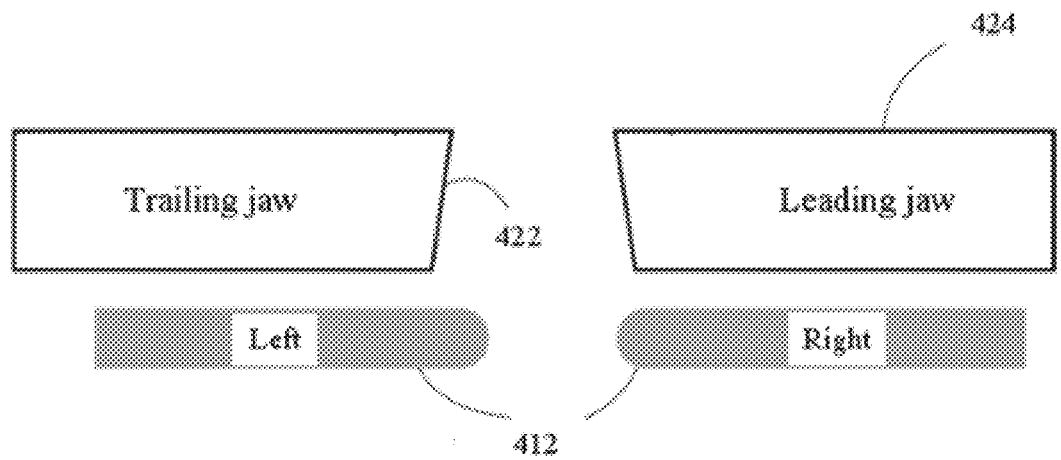
Figure 4C:
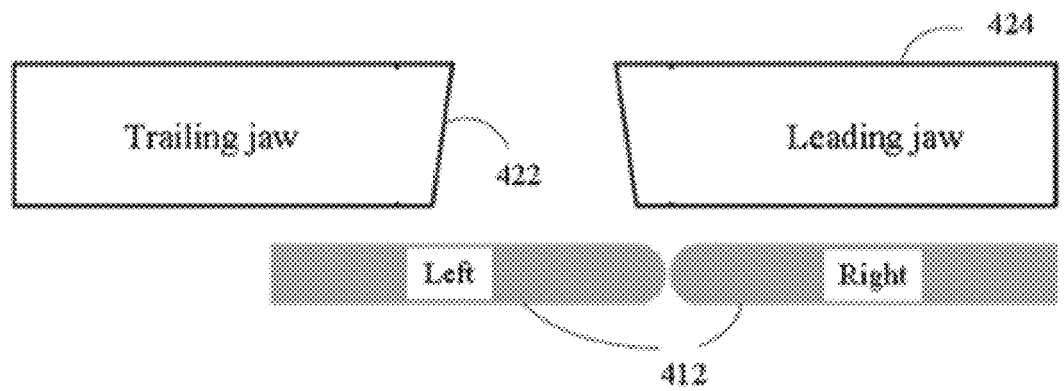

FIGS. 4(a)-4(c) illustrate exemplary relative positions of jaws and a leaf pair of an MLC. As shown in FIGS. 4(a)-4(c), the jaws and the leaf pair may have three positions.

As shown in FIG. 4(a), two leaves of a leaf pair 412 may be closed and a gap may exist between them. The gap may be formed under a trailing jaws 422 and shielded by the trailing jaws 422 to block extra irradiation from leaking through the gap between the leaves. The leaf pair 412 may be positioned like this before points in the corresponding row are irradiated.

As shown in FIG. 4(b), the two leaves of the leaf pair 412 may be opened, and an aperture may exist between them. The aperture may be formed by controlling the leaves and positions of the leading jaws 424 and the trailing jaws 422. The leaf pair 412 may be positioned like this when points in the corresponding row are irradiated.

As shown in FIG. 4(c), the two leaves of the leaf pair 412 may be closed, and a gap may exist between them. The gap may be formed under the leading jaws 424 and shielded by the leading jaws 424 to block extra irradiation from leaking through the gap between the leaves. The leaf pair 412 may be positioned like this after irradiation of points in the corresponding row is completed.

In some embodiments, the CPU 1520 of the MLC 310 may control the movement of the leaves and the jaws, and control the size and positions of the apertures and gaps.

Figure 5A:
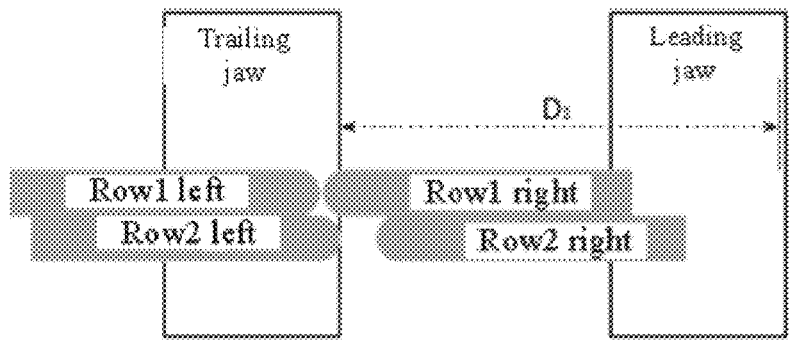
FIGS. 5(a)-5(c) illustrate an exemplary irradiation process based on a fluence map according to some embodiments of the present disclosure.
Figure 5B:
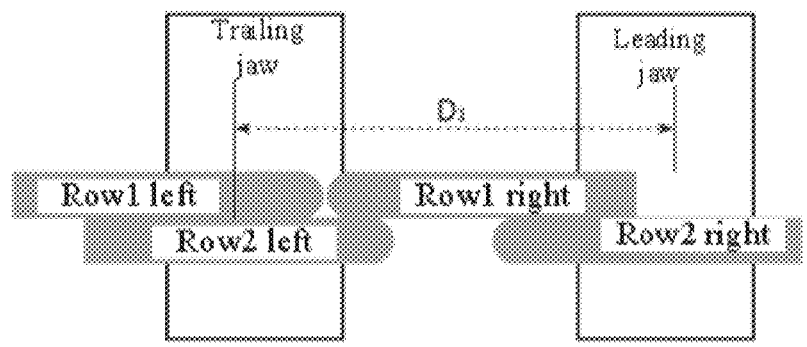
Figure 5C:
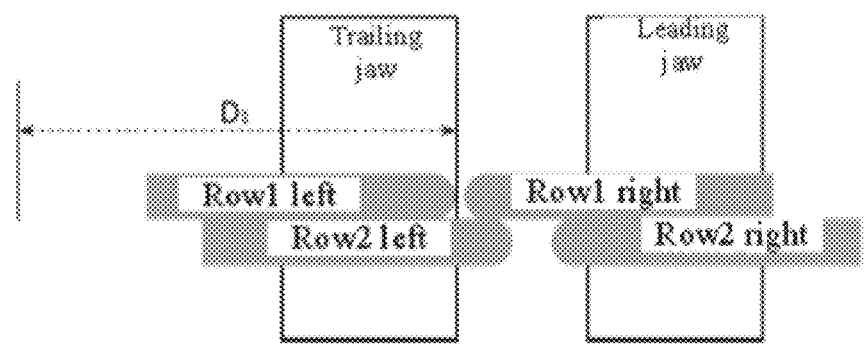

FIGS. 5(a)-5(c) illustrate an exemplary irradiation process based on a fluence map according to some embodiments of the present disclosure. In some embodiments, points in two adjacent rows of the fluence map may start to be irradiated. The two rows may satisfy a condition in FIG. 2(a). The condition may refer to that a horizontal distance $D_1$ between the leftmost points in the two rows is greater than a leaf-span of an MLC. As shown in FIG. 5(a), when the irradiation of the leftmost point 202 in Row 2 of the fluence map is started, a leaf pair corresponding to Row 2 may be positioned like FIG. 4(b). As the distance $D_1$ is greater than the leaf-span, no point in Row 1 should be irradiated within the leaf-span, and a leaf pair corresponding to Row 1 may be positioned like FIG. 4(a). Specifically, two leaves of the leaf pair corresponding to Row 1 may be closed, and a gap may exist between them. The gap may be positioned under the trailing jaw to block extra irradiation from leaking through the gap between the leaves. As shown in FIG. 5(b), when points in Row 2 are irradiated and the leftmost point 201 in Row 1 is not irradiated, the leaf pair corresponding to Row 2 may be still positioned like FIG. 4(b) and the leaf pair corresponding to Row 1 may be still positioned like FIG. 4(a). As shown in FIG. 5(c), when the trailing jaw reaches the initial irradiation point (the leftmost point 201) of Row 1, the gap of the leaf pairs corresponding to Row 1 may be positioned at the right edge of the trailing jaw. The two leaves of the leaf pair corresponding to Row 1 may be opened. Points in Row 1 may be irradiated in the beam field.

The irradiation process in Row 3 and Row 4 of FIG. 2(b) is similar to that in Row 1 and Row 2 of FIG. 2(a), and the detailed description will not repeated here.

Figure 6:
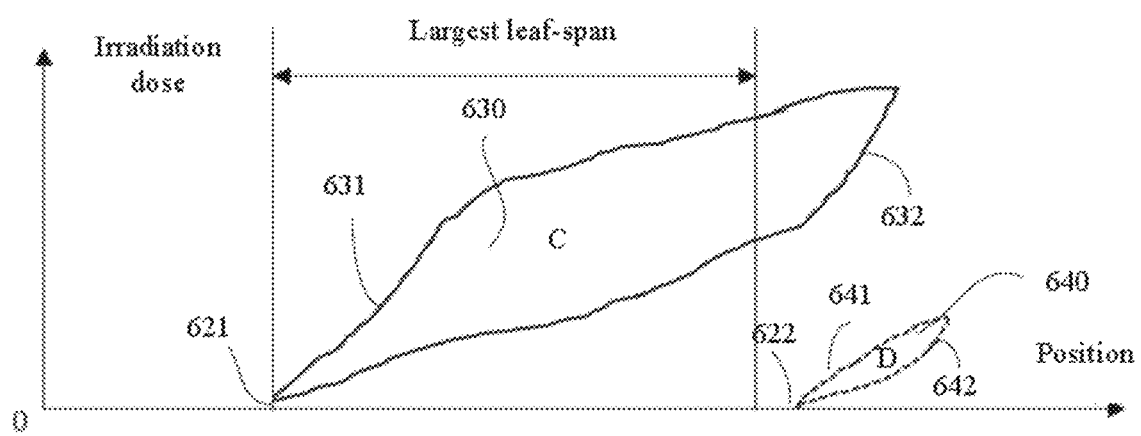
FIG. 6 illustrates exemplary movement curves according to some embodiments of the present disclosure.

FIG. 6 illustrates exemplary movement curves according to some embodiments of the present disclosure. In the movement curves shown in FIG. 6, the movement curve 630 (solid line) and the movement curve 640 (dash line) correspond to Row 8 and Row 4, respectively. Assuming the leaves move from left to right, line 631 and line 632 may correspond to movement trajectories of left leaf and right leaf of the leaf pair in Row 8, respectively. Similarly, line 641 and line 642 may correspond to movement trajectories of left leaf and right leaf of the leaf pair in Row 4, respectively. The area C defined by line 631 and line 632 may be related to irradiation doses of Row 8. The area D defined by line 641 and line 642 may be related to irradiation doses of Row 4. As shown in FIG. 6, a horizontal distance between initial points 621 in the movement curve 630 and initial points 622 in the movement curve 640 is greater than the largest leaf-span. Thus, the two initial points 621 and 622 should not be irradiated simultaneously. For example, in the case that the leaves move from left to right, when irradiation of the initial irradiation point 621 in Row 8 is started, no point in Row 4 should be irradiated within the largest leaf-span. In this case, the leaves of the leaf pair corresponding to Row 4 may be closed and a gap may exist between them. The gap may be shielded by the trailing jaw to block extra irradiation from leaking through the gap. Thus, the shield type of the fluence map of FIG. 1 may be determined in step 1001 as SS-NES selected from the four shield types.

Figure 7A:
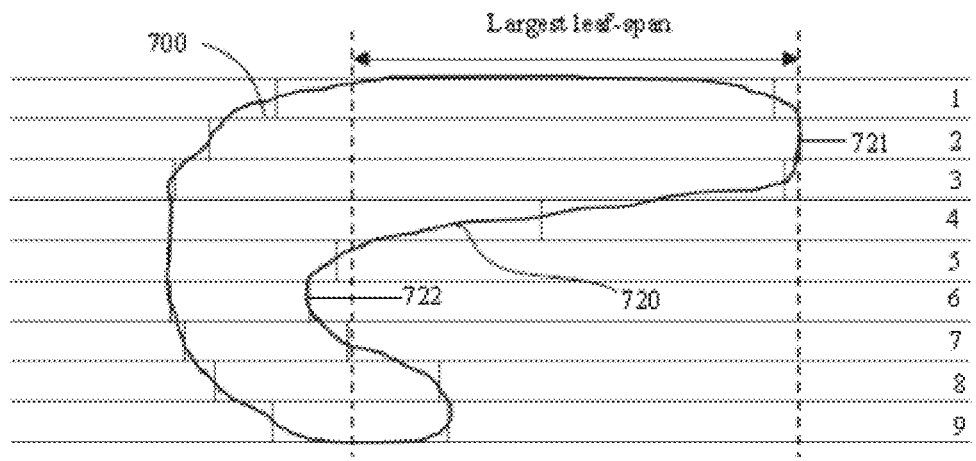
FIG. 7(a) is an exemplary schematic diagram of a fluence map of a subject according to some embodiments of the present disclosure.
Figure 7B:
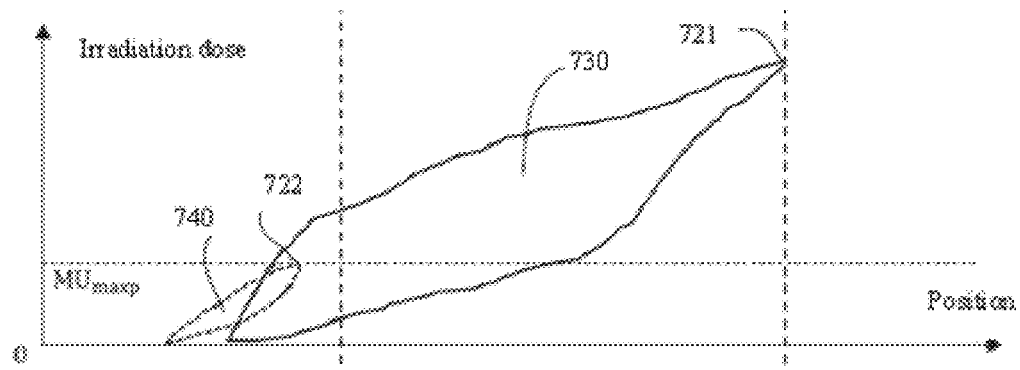
FIG. 7(b) illustrates exemplary movement curves according to some embodiments of the present disclosure.

FIG. 7(a) is an exemplary fluence map of a subject according to some embodiments of the present disclosure. The fluence map may be a fluence map like FIG. 1 after rotating for 180 degrees. FIG. 7(b) illustrates exemplary movement curves according to some embodiments of the present disclosure. In the movement curves shown in FIG. 7(b), the movement curve 730 (solid line) and the movement curve 740 (dash line) correspond to Row 2 and Row 6, respectively. Lines in FIG. 7(b) may be similar to the lines in FIG. 6, and the detailed description thereof will not repeated here. As shown in FIG. 7(b), the horizontal distance between terminal points 721 in the movement curve 730 and 722 in the movement curve 740 is greater than the largest leaf-span. Thus, the irradiation of the two terminal points 711 and 712 should not be completed simultaneously. Assuming the leaves may move from left to right, when irradiation of the terminal irradiation points 722 is completed, the leaf pair corresponding to Row 6 may be closed and a gap may exist between them. The left edge of the leading jaw may move to the terminal irradiation point of the Row 6. The gap may be shielded by the leading jaw to block extra irradiation from leaking through the gap. The leading jaw moves along the movement direction of the leaf pair until the left edge of the leading jaw reaches to the rightmost dash line. The shield type of the fluence map of FIG. 7 may be determined in step 1001 as NSS-ES selected from the four shield types.

As described elsewhere in this disclosure in connection with step 1003, the initial irradiation dose corresponding to a movement curve may not be set to 0 for a row that being shielded at the start of irradiation (e.g., Row 4 in FIG. 6). In some embodiments, irradiation of the initial/terminal irradiation points may not be started/completed simultaneously. The corresponding leaf pair may be shielded by the trailing/leading jaw at the start/end of irradiation. With respect to the above conditions, the movement curves of leaf pairs corresponding to rows may be synchronized.

Figure 12:
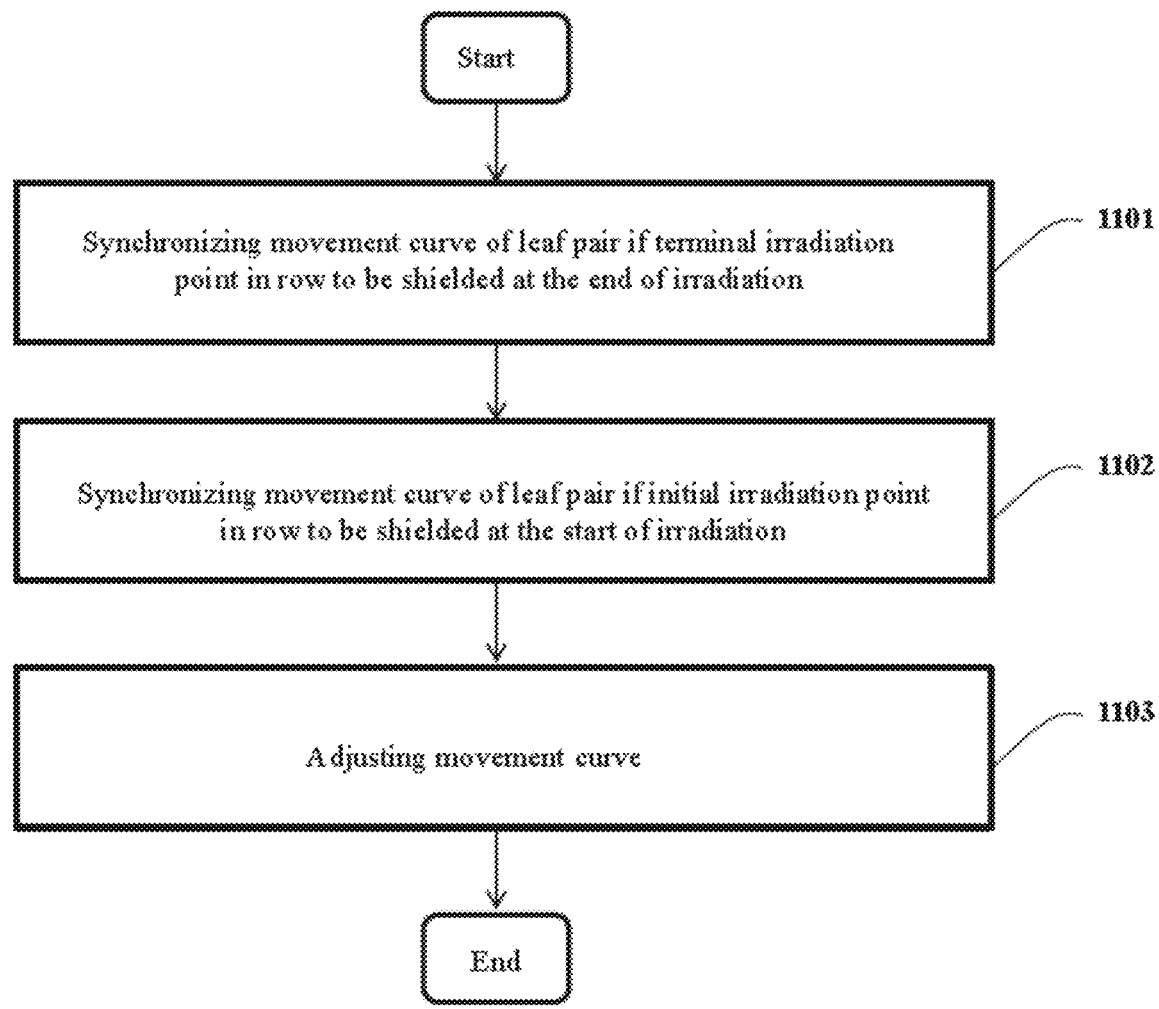
FIG. 12 is a flowchart of an exemplary method of synchronizing movement curves according to some embodiments of the present disclosure.

FIG. 12 is a flowchart of an exemplary method of synchronizing movement curves according to some embodiments of the present disclosure.

In step 1101, one or more movement curves corresponding to leaf pairs may be synchronized if a terminal irradiation point (the rightmost point) in a row needs to be shielded at the end of irradiation.

For a terminal irradiation point in a row in the movement direction of the jaws and the MLC 310, if irradiation of the terminal irradiation point in the row is completed, the leaf pair corresponding to the row may be closed and a gap may exist between them. The gap of the leaf pair may be shielded. The terminal maximum monitor unit ($MU_{maxp}$) of the movement curve of the corresponding leaf pair may be set as a required minimum monitor unit of movement curves of all leading leaves reaching to the point. The movement curve may be adjusted in step 1103 according to a result of the synchronization.

Figure 7C:
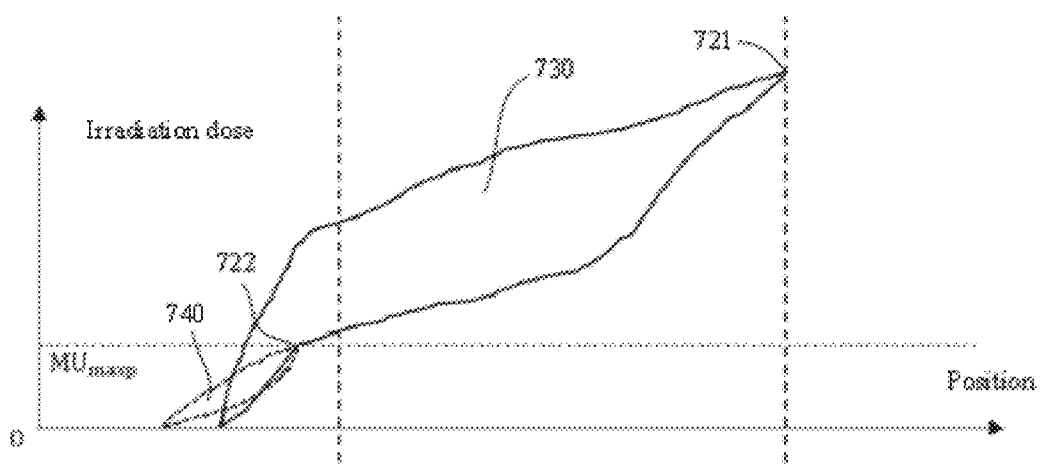
FIG. 7(c) illustrates exemplary synchronized movement curves according to some embodiments of the present disclosure.

Take the movement curves in FIG. 7(b) as an example. As described elsewhere in this disclosure in connection with FIG. 7b, when irradiation of the terminal irradiation point 722 is finished, a gap between the leaf pair corresponding to Row 6 may be shielded by the leading jaw. In this case, the required monitor unit of movement curves of any other leaves that reaching to the terminal irradiation point 722 should be greater than or equal to the terminal monitor unit ($MU_{maxp}$) of movement curve 740 in Row 6. FIG. 7(c) illustrates exemplary synchronized movement curves according to some embodiments of the present disclosure. As shown in FIG. 7(c), the required monitor unit (MU) of the movement curve 730 may be greater than or equal to the terminated monitor unit ($MU_{maxp}$) of movement curve 740 in Row 6. The synchronized movement curve 730 may be determined.

In step 1102, one or more movement curves corresponding to leaf pairs may be synchronized if an initial irradiation point (the leftmost point) in a row needs to be shielded at the start of irradiation.

In some embodiments, an initial irradiation point in a row may be on the movement direction of the jaws and the MLC. If irradiation of the initial irradiation point in the row is not started, the leaf pair corresponding to the row may be closed and a gap may exist between them. The gap of the leaf pair corresponding to the row should be shielded to block extra irradiation from leaking through the gap. In this case, an initial monitor unit (irradiation dose) may not be set to 0. Exemplary method for determining initial maximum monitor unit ($MU_{maxt}$, or referred to as initial irradiation dose) can be found elsewhere in this disclosure in connection with step 1003. At the start of irradiation, a required initial maximum monitor unit ($MU_{maxt}$) at the point may be determined. The initial maximum irradiation dose of all leaf pairs at the point may be set to the initial maximum monitor unit ($MU_{maxt}$). In some embodiments, the CPU 1520 or other calculation components of the MLC 310 may determine the initial irradiation doses. In some embodiments, a user may provide the initial irradiation doses via the I/O component 1560.

Figure 8A:
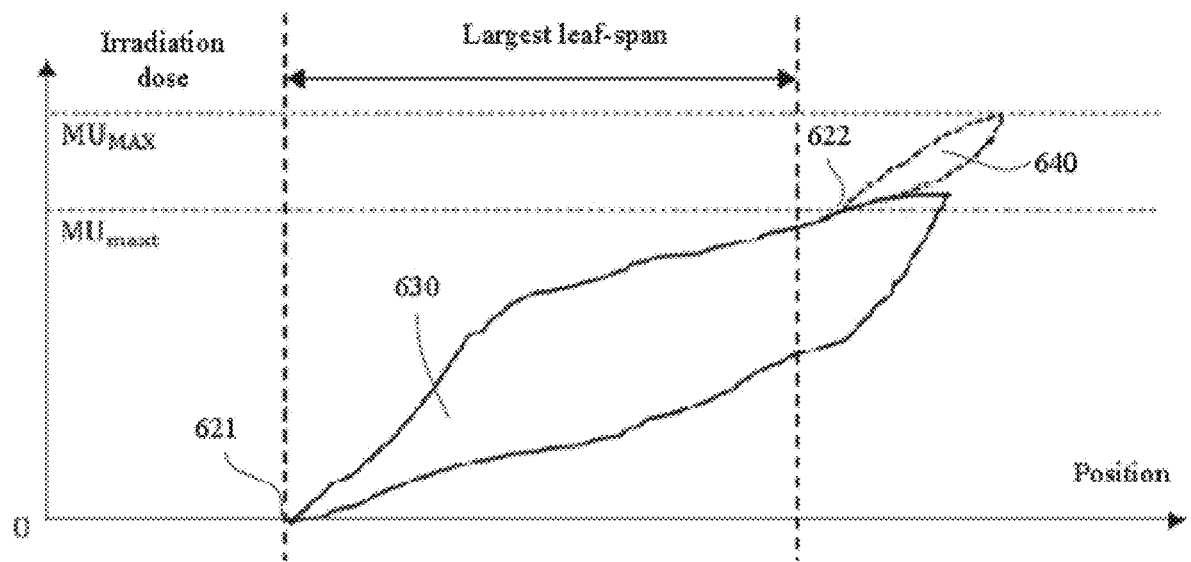
FIGS. 8(a) and 8(b) illustrate exemplary synchronized movement curves according to some embodiments of the present disclosure.
Figure 8B:
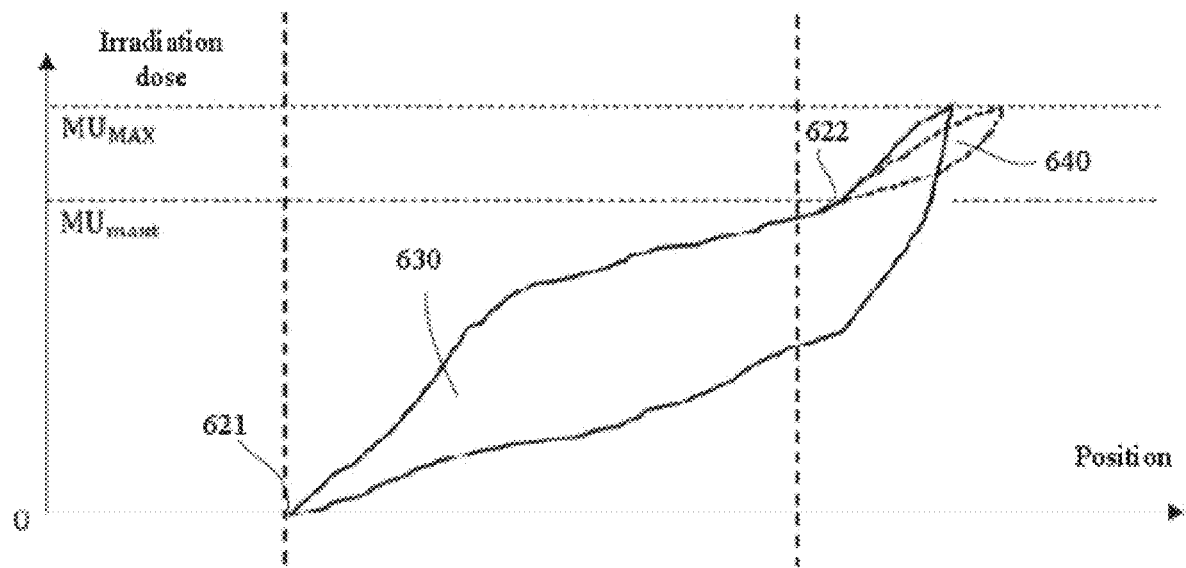

FIGS. 8(a) and 8(b) illustrate exemplary synchronized movement curves according to some embodiments of the present disclosure. As shown in FIG. 8(a), the initial monitor unit of the movement curve 640 may be set to the initial maximum monitor unit ($MU_{maxt}$). As shown in FIG. 8(b), when the trailing leaf corresponding to Row 8 reaches the initial irradiation point 622 in Row 4, the required maximum monitor unit (MU) of the movement curve 630 may be set to the initial maximum monitor unit ($MU_{maxt}$) of the movement curve 640. The synchronized movement curve 630 may be determined.

In step 1103, the movement curve may be adjusted. If the leaf pairs corresponding to the rows are not shielded at the end of irradiation, the terminal irradiation doses of movement curves of all the leaf pairs may be set to a same value. Alternatively or additionally, if the leaf pairs corresponding to the rows are not shielded at the start of irradiation, the initial irradiation doses of movement curves of all the leaf pairs may be set to a same value. For example, as shown in FIG. 8(b), the terminal irradiation doses corresponding to movement curves 630 and 640 are both set to $MU_{max}$.

It can be understood that, in some embodiments, any or all of the steps 1101, 1102 and 1103 may be optional. In some embodiments, the CPU 1520 of the MLC 310 may perform the synchronization process. In some embodiments, the disk 1570, ROM 230, and/or RAM 240 may store the synchronized movement curve. In some embodiments, the computing device 1500 may transmit the synchronized movement curve to a user via the I/O component 1560.

Figure 13:
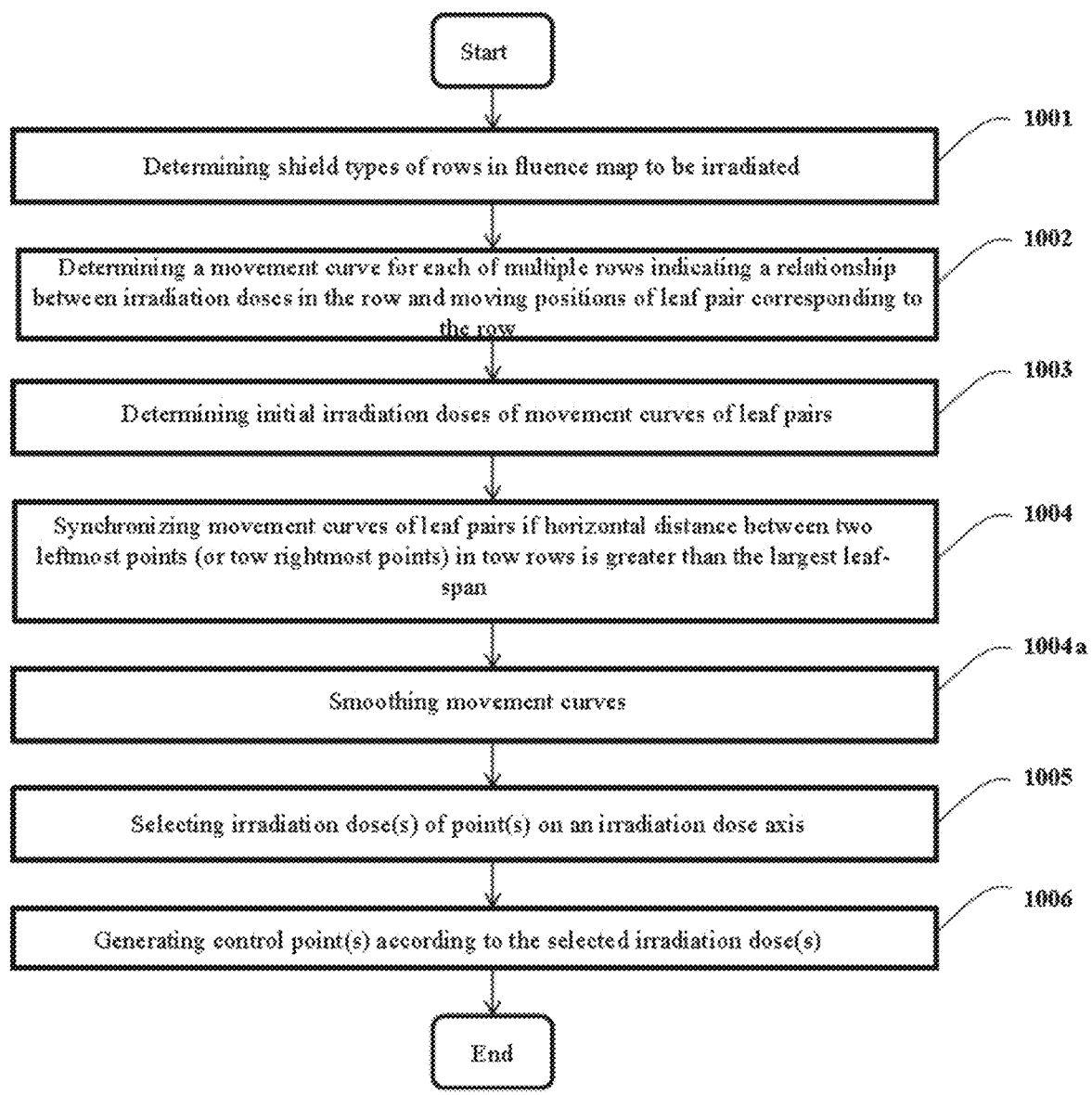
FIG. 13 is a flowchart of an exemplary irradiation method based on a fluence map according to some embodiments of the present disclosure.

FIG. 13 is a flowchart of an exemplary irradiation method of a fluence map according to some embodiments of the present disclosure. In order to avoid dramatic changes of movement speeds of the leaves, a step 1004a, as shown in FIG. 13, may be added after step 1004 to smooth the movement curves. In some embodiments, the CPU 1520 of the MLC 310 may perform the smoothness process.

The required control point(s) during irradiation process may be determined after processed in connection with FIG. 11 and/or FIG. 13.

Figure 9A:
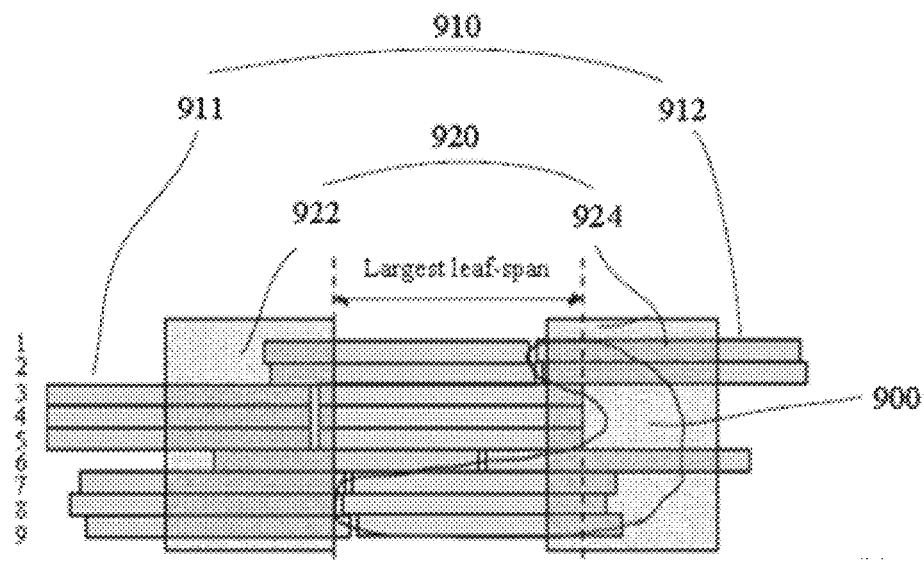
FIGS. 9(a)-9(d) illustrate exemplary positions and movements of jaws and leaves during an irradiation process according to some embodiments of the present disclosure.
Figure 9B:
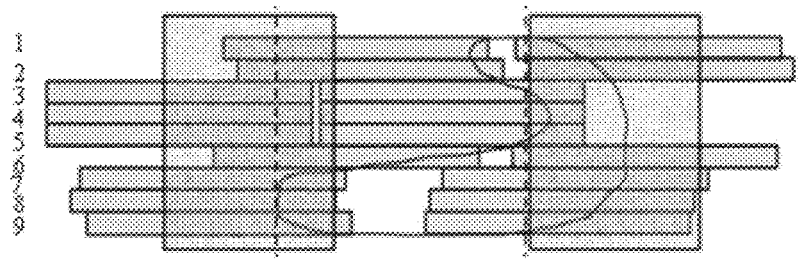
Figure 9C:
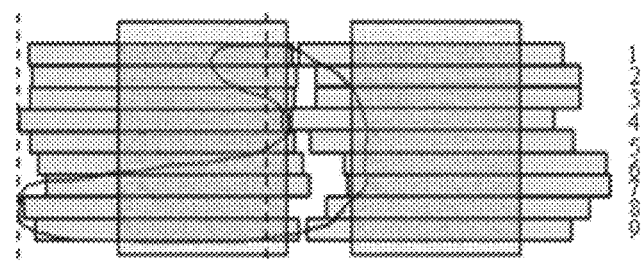
Figure 9D:
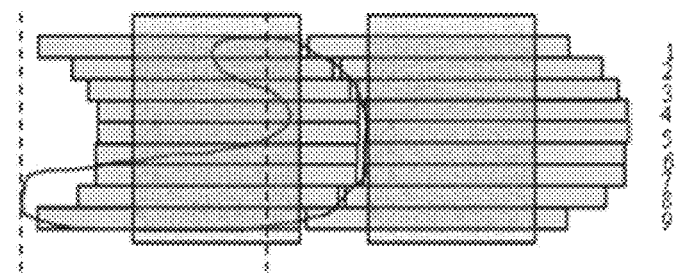
Figure 10A:
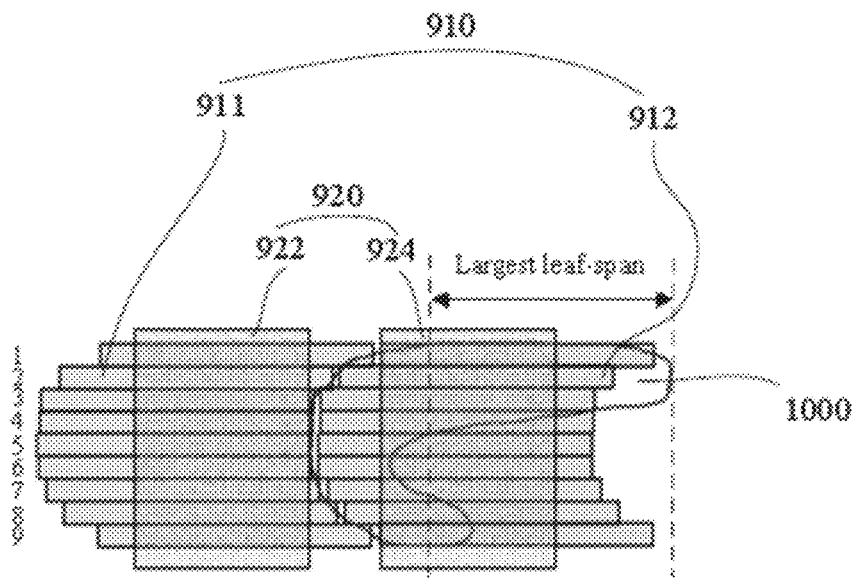
FIGS. 10(a)-10(d) illustrate exemplary positions and movements of jaws and leaves during an irradiation process according to some embodiments of the present disclosure.
Figure 10B:
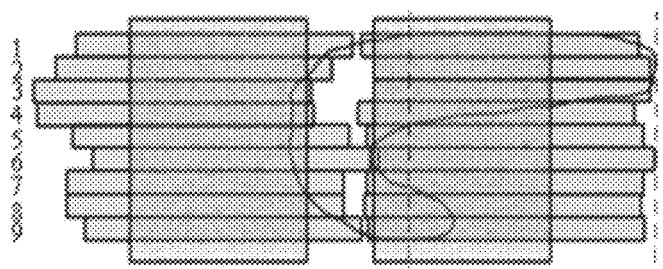
Figure 10C:
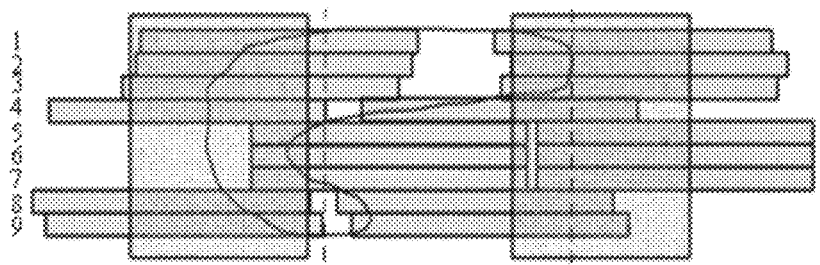
Figure 10D:
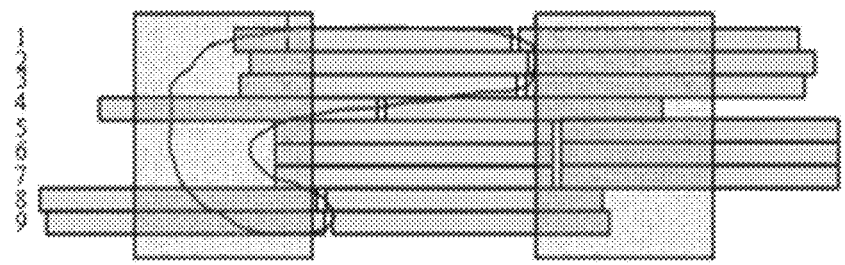

FIG. 9(a)-9(d) illustrate exemplary positions and movements of jaws and leaves during an irradiation process according to some embodiments of the present disclosure. The fluence map 900 may correspond to the fluence map 100 in FIG. 1. As shown in FIG. 9, an MLC may include a plurality of leaves 911 on the left (or referred to as left leaves) and a plurality of leaves 912 on the right (or referred to as right leaves). And the leaves in each row may form a leaf pair 910. Parallel jaws 920 may include a trailing jaw 922 and a leading jaw 924. The top and bottom portions out of the contour of the fluence map may be shielded by the perpendicular jaws 920. Take Row 3, Row 4, Row 5, and Row 8 as an example. As shown in FIG. 9(a), at the start of irradiation, the right edge of the trailing jaw 922 may be positioned at the leftmost point in Row 8 of the fluence map 900. The leaf pairs corresponding to Row 3, Row 4, and Row 5 of the fluence map 900 may be closed and gaps may be formed, respectively. The gaps may be shielded by the trailing jaw 922. In this case, the initial irradiation point (the leftmost point) in Row 8 may be irradiated at first. Then, as shown in FIG. 9(b), the leaves of the MLC and the jaws may gradually move rightward. The gaps between corresponding leaf pairs corresponding to Row 3, Row 4 and Row 5 may be shielded by the trailing jaw 922. An aperture may be formed by controlling a leaf pair and the positions of the leading jaw 924 and the trailing jaw 922. Points in any other row may be irradiated gradually through the apertures defined by the corresponding leaf pairs. Next, as shown in FIG. 9(c), with the movement of the leaves of the MLC and the jaws, the right edge of the trailing jaw 922 may be positioned at the leftmost point in Row 4 of the fluence map 900. The gap of the leaf pair corresponding to Row 4 may start to move out from under the trailing jaw 922, and points in other rows may be irradiated continuously through the apertures defined by the corresponding leaf pairs. The irradiation of points in Row 1 and Row 9 may be almost completed. Finally, as shown in FIG. 9(d), all the leaf pairs may be closed and gaps may be formed. All the gaps of the corresponding leaf pairs may be positioned at the terminal irradiation points (the rightmost points).

In some embodiments, the CPU 1520 of the MLC 310 may control the movement of the leaves and the jaws and hence control the size and positions of the apertures and gaps.

According to the description in FIG. 9, a fluence map may include at least a fluence area with a first row (such as Row 8 in FIG. 9) and a fluence area with a second row (such as Row 3 row in FIG. 9). There may be a horizontal distance between leftmost points (or rightmost points) in the two rows that is greater than a leaf-span. The first row of fluence area and the second row of fluence area may each include an initial irradiation point and a terminal irradiation point. If the horizontal distance between the initial irradiation points in the first row of fluence area and the second row of fluence area is greater than a leaf-span of an MLC, the irradiation method may include one or more steps.

An initial irradiation point in one of the first row and the second row may start to be irradiated earlier than the other. The corresponding row may be referred to as an earlier irradiation-started row (e.g., Row 8). The other row may be referred to as a later irradiation-started row (e.g. Row 3). The gap of the leaf pair corresponding to the earlier irradiation-started row may be positioned at the initial irradiation point of the row by moving the corresponding leaf pair.

The right edge of the trailing jaw may be positioned at the initial irradiation point of the earlier irradiation-started row. The trailing jaw may shield the 0-fluence area in the later irradiation-started row when the earlier irradiation-started row is started to be irradiated.

The leaves of the MLC and the jaws may move continuously. An aperture may be formed by controlling the leaf pair of the earlier irradiation-started row and the positions of the two jaws. The points in the earlier irradiation-started row may be irradiated gradually through the aperture defined by the leaf pair. The 0-fluence area of the later irradiation-started row may be shielded until the gap of the leaf pair corresponding to the later irradiation-started row reaches the initial irradiation point of the later irradiation-started row. Then points in the later irradiation-started row may start to be irradiated.

The other fluence areas in the first and second rows may be irradiated by moving and/or controlling the leaf pairs of the first and second rows.

FIG. 10(*a*)-10(*d*) illustrate exemplary positions and movements of jaws and leaves during an irradiation process according to some embodiments of the present disclosure. The fluence map 1000 may correspond to the fluence map 700 in FIG. 7. As shown in FIG. 10(*a*), an MLC may include a plurality of leaves 911 on the left (or referred to as left leaves) and a plurality of leaves 912 on the right (or referred to as right leaves). And the leaves in each row may together form a leaf pair 910. Parallel jaws 920 may include a trailing jaw 922 and a leading jaw 924. The top and bottom portions out of contour of the fluence map may be shielded by the perpendicular jaws 910. Take Row 2, Row 5, Row 6, and Row 7 as an example. As shown in FIG. 10(*a*), at the start of irradiation, the right edge of the trailing jaw 922 may be positioned at the leftmost point in Row 6 of the fluence map 1000. Then, as shown in FIG. 10(*b*), with the movement of the leaves of leaf pairs of the MLC and the jaws, irradiation of points in Row 6 is completed. The two leaves of the leaf pair corresponding to Row 6 may be closed, and a gap may exist between them. The left edge of the leading jaw 924 may be positioned at the rightmost point in Row 6 of the fluence map 1000. In this case, the gap may be positioned under the leading jaw 924 and be shielded by the leading jaw 924 to block extra irradiation from leaking through the gap. At the same time, an aperture may be formed by controlling the leaf pair of Row 2 and the positions of the leading jaw 924 and the trailing jaw 922. Points in Row 2 may be irradiated continuously through the aperture defined by the corresponding leaf pair. Next, as shown in FIG. 10(*c*), the leaves of the MLC and the jaws may continuously move rightward. irradiation of points in Row 5, Row 6 and Row 7 is completed. The leaves of the leaf pairs corresponding to Row 5, Row 6 and Row 7 may be closed respectively and gaps may be formed respectively. The gaps may be positioned under the leading jaw 924 and be shielded by the leading jaw 924 to block extra irradiation from leaking through the gaps. At the same time, Points in Row 2 may be continuously irradiated through the aperture defined by the corresponding leaf pair. Finally, as shown in FIG. 10(*d*), the left edge of the leading jaw 924 may be positioned at the rightmost in Row 2 of the fluence map 1000. In this case, irradiation of points in Row 2 is completed, specifically, irradiation of points in all the rows are completed. All the leaf pairs may be closed and gaps may be formed.

In some embodiments, the CPU 1520 of the MLC 310 may control the movement of the leaves and the jaws and hence control the size and positions of the apertures and gaps.

According to the description in FIG. 10, a fluence map may include at least a fluence area with a first row (such as Row 6 in FIG. 10) and a fluence area with a second row (such as Row 2 in FIG. 10). There may be a horizontal distance between leftmost points (or rightmost points) in the two rows that is greater than a leaf-span. The first row of fluence area and the second row of fluence area may each include an initial irradiation point and a terminal irradiation point. If the horizontal distance between the terminal irradiation points in the row of fluence area and the second row of fluence area is greater than a leaf-span of an MLC, the irradiation method may include one or more steps.

A terminal irradiation point in one of the first row and the second row may finish to be irradiated earlier than the other. The corresponding row may be referred to as an earlier irradiation-completed row (e.g., Row 6). The other row may be referred to as a later irradiation-completed row (e.g., Row 2). The gap of the leaf pair corresponding to the earlier irradiation-completed row may be positioned at the terminal irradiation point of the row.

The left edge of the leading jaw may be positioned at the terminal irradiation point of the earlier irradiation-completed row. The leading jaw may shield the 0-fluence area in the earlier irradiation-completed row when the earlier irradiation-completed row is completed to be irradiated.

The leaves of the MLC and the jaws may move continuously. An aperture may be formed by controlling the leaf pair of the later irradiation-completed row and the positions of the two jaws. The points in the later irradiation-completed row may be irradiated gradually through the aperture defined by the leaf pair. The 0-fluence area of the earlier irradiation-completed row may be shielded until the gap of the leaf pair corresponding to later irradiation-completed row reaches the terminal irradiation point of the later irradiation-completed row. The irradiation of points in the later irradiation-completed row may be completed.

It could be understood that, in some embodiments, a fluence map may just refer to a fluence map shown in FIG. 9. Leaves of leaf pairs may be shielded at the start of irradiation. In some embodiments, a fluence map may just refer to a fluence map shown in FIG. 10. Leaves of leaf pairs may be shielded at the end of irradiation. In some embodiments, a fluence map may refer to a combination of fluence maps shown in FIG. 9 and FIG. 10. Leaves of leaf pairs may be shielded at the start and end of irradiation.

Figure 14:
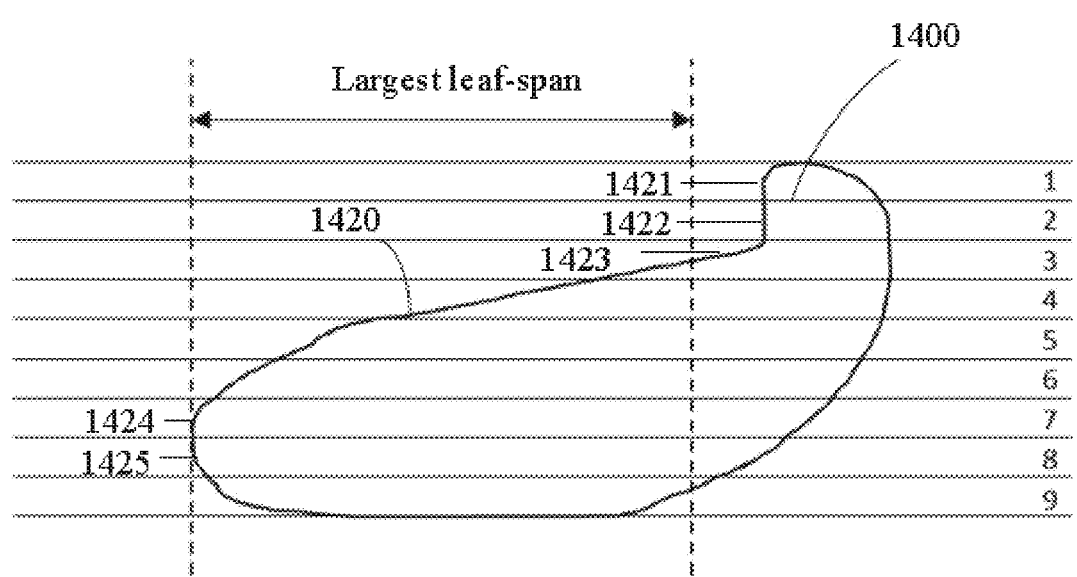
FIG. 14 is a flowchart of an exemplary fluence map of a subject according to some embodiments of the present disclosure.

FIG. 14 is a schematic diagram of an exemplary fluence map of a subject according to some embodiments of the present disclosure. The subject may be same with the subject disclosed in FIG. 1, such as a tissue, an organ, a tumor, etc.

As shown in FIG. 14, in the left contour 1420 of the fluence map 1400, the horizontal distance between the initial irradiation point 1421 in Row 1 (or the initial irradiation point 1422 in Row 2, or the initial irradiation point 1423 in Row 3) and the initial irradiation point 1424 in Row 7 (or the initial irradiation point 1425 in Row 8) may be greater than the largest leaf-span of an MLC. Thus, the above-mentioned methods may be used to implement irradiation of points in the fluence map 1400. Specifically, leaf pairs corresponding to Row 1, Row 2, and/or Row 3 may be shielded by a trailing jaw. As shown in FIG. 14, the initial irradiation points 1421, 1422, and/or 1423 may be positioned at a perpendicular direction with respect to the movement direction of leaves. At the start of irradiation, a perpendicular jaw may be used to shield the leaves corresponding to these rows without affecting the irradiation of points in other rows. The shielding by using the perpendicular jaw may be similar to that by using the paralleling jaw, and detailed description thereof will not be repeated here.

In some embodiments, there may be a horizontal distance between points on the left contour (or right contour) of a fluence map that is greater than a leaf-span. In the present disclosure, by using parallel jaws to assist an MLC, irradiation of the points in rows of the fluence map may be implemented without dividing a beam field. However, if horizontal distances between all points in rows of a fluence map are not greater than a leaf-span, the irradiation method of the present disclosure may also be used. Specifically, one or more leaf pairs may be shield by the parallel jaws without considering whether the above condition is satisfied.

It can be understood by one of skilled in the art that, the jaws herein can be replaced by other blocks. The blocks should be moveable and not transparent to X-rays.

Although the present disclosure may be described in accordance with the above specific embodiments. It should be noted that the above description of the method and system for irradiation is provided for the purposes of illustration, and not intended to limit the scope of the present disclosure. For persons having ordinary skills in the art, the method and system may be modified or substituted under the teaching of the present disclosure. However, those modifications or substitutions are within the protection scope of the present disclosure.

I claim:

1. A method for controlling a multi-leaf collimator (MLC) and a plurality of jaws, the method being implemented on a computing device having at least one processor, and at least one computer-readable storage medium, wherein:
the MLC includes a plurality of leaf pairs, each of the plurality of leaf pairs comprising a left leaf and a right leaf, and the method includes:
obtaining a fluence map including a plurality of rows, wherein each of the plurality of rows corresponds to one of the plurality of leaf pairs, and a distance between a first edge point of each of one or more first rows of the plurality of rows and a second edge point of each of one or more second rows of the plurality of rows is greater than a distance threshold; and
irradiating a portion of multiple irradiation points in the one or more first rows, while shielding irradiation leaking through a zero-fluence area of each of the one or more second rows by a jaw and one or more second leaf pairs corresponding to the one or more second rows.

2. The method of claim 1, wherein the distance threshold includes a difference between a longest length of extension and a shortest length of extension of left leafs of the plurality of leaf pairs or right leafs of the plurality of leaf pairs.

3. The method of claim 1, wherein at the start of an irradiation, the one or more second rows are shielded while the one or more first rows are not shielded and at the end of the irradiation both the one or more first rows and the one or more second rows are not shielded.

4. The method of claim 1, wherein the irradiating a portion of multiple irradiation points in the one or more first rows includes:
moving the one or more first leaf pairs to a first initial irradiation point of the one or more first leaf pairs; and
moving the one or more first leaf pairs to irradiate the portion of multiple irradiation points in the one or more first rows.

5. The method of claim 4, wherein the shielding irradiation leaking through a zero-fluence area of each of the one or more second rows by a jaw and one or more second leaf pairs corresponding to the one or more second rows includes:
moving the jaw to the first initial irradiation point of the one or more first leaf pairs;
closing the one or more second leaf pairs and forming a gap between each of the one or more second leaf pairs; and
moving the jaw and the one or more second leaf pairs along with the one or more first leave pairs, and
shielding the gap between each of the one or more second leaf pairs by the jaw.

6. The method of claim 5, further comprising:
irradiating a portion of multiple irradiation points in the one or more second rows until an edge of the jaw reaches a second edge point of the one or more second rows.

7. The method of claim 6, wherein the irradiating a portion of multiple irradiation points in the one or more second rows until an edge of the jaw reaches a second edge point of the one or more second rows includes:
moving the one or more second leaf pairs out from the jaw; and
moving the one or more second rows to irradiate the portion of the multiple irradiation points in the one or more second rows.

8. The method of claim 1, further comprising:
simultaneously irradiating multiple irradiation points of remaining rows other than the one or more first rows and the one or more second rows of the plurality of rows.

9. The method of claim 1, wherein at the start of an irradiation, both the one or more first rows and the one or more second rows are not shielded and at the end of the irradiation the one or more second rows are shielded while the one or more first rows are not shielded.

10. The method of claim 9, before the irradiating a portion of multiple irradiation points in the one or more first rows, the method comprising:
irradiating a portion of multiple irradiation points in the one or more second rows.

11. The method of claim 10, wherein the shielding irradiation leaking through a zero-fluence area of each of the one or more second rows by a jaw and one or more second leaf pairs corresponding to the one or more second rows includes:
closing one or more second leaf pairs corresponding to the one or more second rows of the plurality of leaf pairs and forming a gap between each of the one or more second leaf pairs;

moving an edge of the jaw to a second edge point of the one or more second rows; and shielding the gap between each of the one or more second leaf pairs.

12. The method of claim 11, wherein the irradiating a portion of multiple irradiation points in the one or more first rows includes:

moving the one or more first leaf pairs to irradiate the portion of the multiple irradiation points of in the first row.

13. The method of claim 12, further comprising:

simultaneously irradiating irradiation points of remaining rows other than the one or more first rows and the one or more second rows of the plurality of rows.

14. The method of claim 1, wherein at the start of an irradiation, the one or more second rows are shielded while the one or more first rows are not shielded and at the end of the irradiation the one or more second rows are shielded while the one or more first rows are not shielded.

15. The method of claim 14, further comprising:

irradiating multiple irradiation points in the one or more second rows; and irradiating a second portion of the multiple irradiation points in the one or more first rows after complete irradiation of the multiple irradiation points in the one or more second rows, while shielding second irradiation leaking through a second zero-fluence area of each of the one or more second rows by a second jaw and the one or more second leaf pairs.

16. The method of claim 1, wherein:

the first edge point includes a leftmost point of a first row, the second edge point includes a leftmost point of a second row, and the edge of the jaw includes a right edge of the jaw; or the second edge point includes a rightmost point of a second row, and the edge point of the second row includes a rightmost point of the second row, and the edge of the jaw includes a left edge of the jaw.

17. The method of claim 1, wherein the jaw includes a trailing jaw or a leading jaw.

18. The method of claim 15, wherein the second jaw includes a trailing jaw or a leading jaw.

19. A system, comprising:

at least one storage device including a set of instructions for controlling a multi-leaf collimator (MLC) and a plurality of jaws, wherein:

the MLC includes a plurality of leaf pairs, each of the plurality of leaf pairs comprising a left leaf and a right leaf, and at least one processor in communication with the at least one storage device, wherein when executing the set of instructions, the at least one processor is configured to cause the system to perform operations including:

obtaining a fluence map including a plurality of rows, wherein each of the plurality of rows corresponds to one of the plurality of leaf pairs, and a distance between a first edge point of each of one or more first rows of the plurality of rows and a second edge point of each of one or more second rows of the plurality of rows is greater than a distance threshold; and irradiating a portion of multiple irradiation points in the one or more first rows, while shielding irradiation leaking through a zero-fluence area of each of the one or more second rows by a jaw and one or more second leaf pairs corresponding to the one or more second rows.

20. The system of claim 19, wherein the distance threshold includes a difference between a longest length of extension and a shortest length of extension of left leafs of the plurality of leaf pairs or right leafs of the plurality of leaf pairs.

* * * * *